United States Patent
Prince

(10) Patent No.: US 8,939,074 B2
(45) Date of Patent: Jan. 27, 2015

(54) COLOR-BASED LINEAR THREE DIMENSIONAL ACQUISITION SYSTEM AND METHOD

(71) Applicant: David P. Prince, Wakefield, RI (US)

(72) Inventor: David P. Prince, Wakefield, RI (US)

(73) Assignee: Illinois Tool Works Inc., Glenview, IL (US)

( * ) Notice: Subject to any disclaimer, the term of this patent is extended or adjusted under 35 U.S.C. 154(b) by 44 days.

(21) Appl. No.: 13/796,512

(22) Filed: Mar. 12, 2013

(65) Prior Publication Data

US 2014/0272103 A1    Sep. 18, 2014

(51) Int. Cl.
| | |
|---|---|
| *B05C 17/04* | (2006.01) |
| *B41L 13/18* | (2006.01) |
| *H05K 3/22* | (2006.01) |
| *G01B 11/25* | (2006.01) |
| *H05K 13/04* | (2006.01) |
| *H05K 13/08* | (2006.01) |

(52) U.S. Cl.
CPC ............ *H05K 3/225* (2013.01); *G01B 11/2509* (2013.01); *H05K 13/0469* (2013.01); *H05K 13/08* (2013.01)
USPC ......................................... 101/123; 101/126

(58) Field of Classification Search
USPC .................................................. 101/123, 126
See application file for complete search history.

(56) References Cited

U.S. PATENT DOCUMENTS

| | | | |
|---|---|---|---|
| 6,738,505 | B1 | 5/2004 | Prince |
| 6,891,967 | B2 | 5/2005 | Prince |
| 7,072,503 | B2 | 7/2006 | Prince |
| 7,149,344 | B2 | 12/2006 | Prince |
| 7,310,438 | B2 | 12/2007 | Prince |
| 7,404,861 | B2 | 7/2008 | Prentice et al. |
| 7,458,318 | B2 | 12/2008 | Prince |
| 7,710,611 | B2 | 5/2010 | Prince |
| 2005/0268799 | A1 | 12/2005 | Pham-Van-Diep et al. |
| 2007/0102477 | A1 | 5/2007 | Prince |

(Continued)

FOREIGN PATENT DOCUMENTS

| | | |
|---|---|---|
| EP | 2 196 765 A1 | 6/2010 |
| WO | 01/33933 A1 | 5/2001 |

(Continued)

OTHER PUBLICATIONS

Notification of Transmittal of the International Search Report and the Written Opinion of the International Searching Authority from corresponding PCT/US2014/017225 dated Jun. 13, 2014.

*Primary Examiner* — Ren Yan
(74) *Attorney, Agent, or Firm* — Lando & Anastasi, LLP

(57) ABSTRACT

A system and method for capturing three-dimensional image data for inspection, alignment and operations of a material applicator includes an imaging system configured to capture three-dimensional image data of an electronic substrate. The imaging system includes one or more illumination assembly configured to project a spectrum of light substantially along a first axis at an angle to the surface of the electronic substrate. The imaging system further includes an image sensor assembly configured to detect the spectrum of light reflected from an electronic substrate surface, with the image sensor assembly including a viewing plane. The material application includes a controller that is coupled to the imaging system. The controller is configured to control movement of the imaging system and to communicate with the image sensor assembly to produce a three-dimensional image of the topology of the electronic substrate.

9 Claims, 10 Drawing Sheets

(56) References Cited

U.S. PATENT DOCUMENTS

| | | | |
|---|---|---|---|
| 2007/0183645 A1* | 8/2007 | Beaty et al. | 382/145 |
| 2007/0299338 A1* | 12/2007 | Stevick et al. | 600/425 |
| 2008/0156207 A1 | 7/2008 | Ellenbogen | |
| 2009/0096994 A1* | 4/2009 | Smits | 353/30 |
| 2011/0102575 A1* | 5/2011 | Case et al. | 348/87 |
| 2013/0133574 A1 | 5/2013 | Doyle et al. | |
| 2013/0136850 A1 | 5/2013 | Doyle et al. | |

FOREIGN PATENT DOCUMENTS

| | | |
|---|---|---|
| WO | 02/082009 A1 | 10/2002 |
| WO | 2010/100571 A1 | 9/2010 |

* cited by examiner

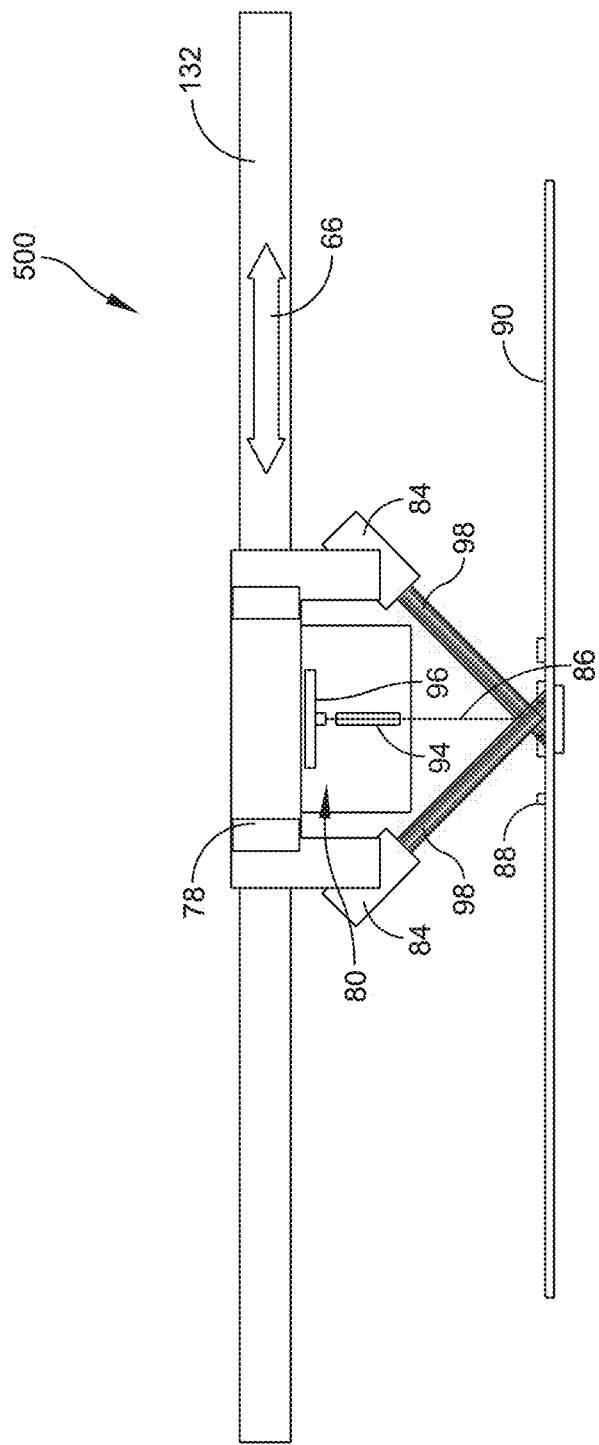

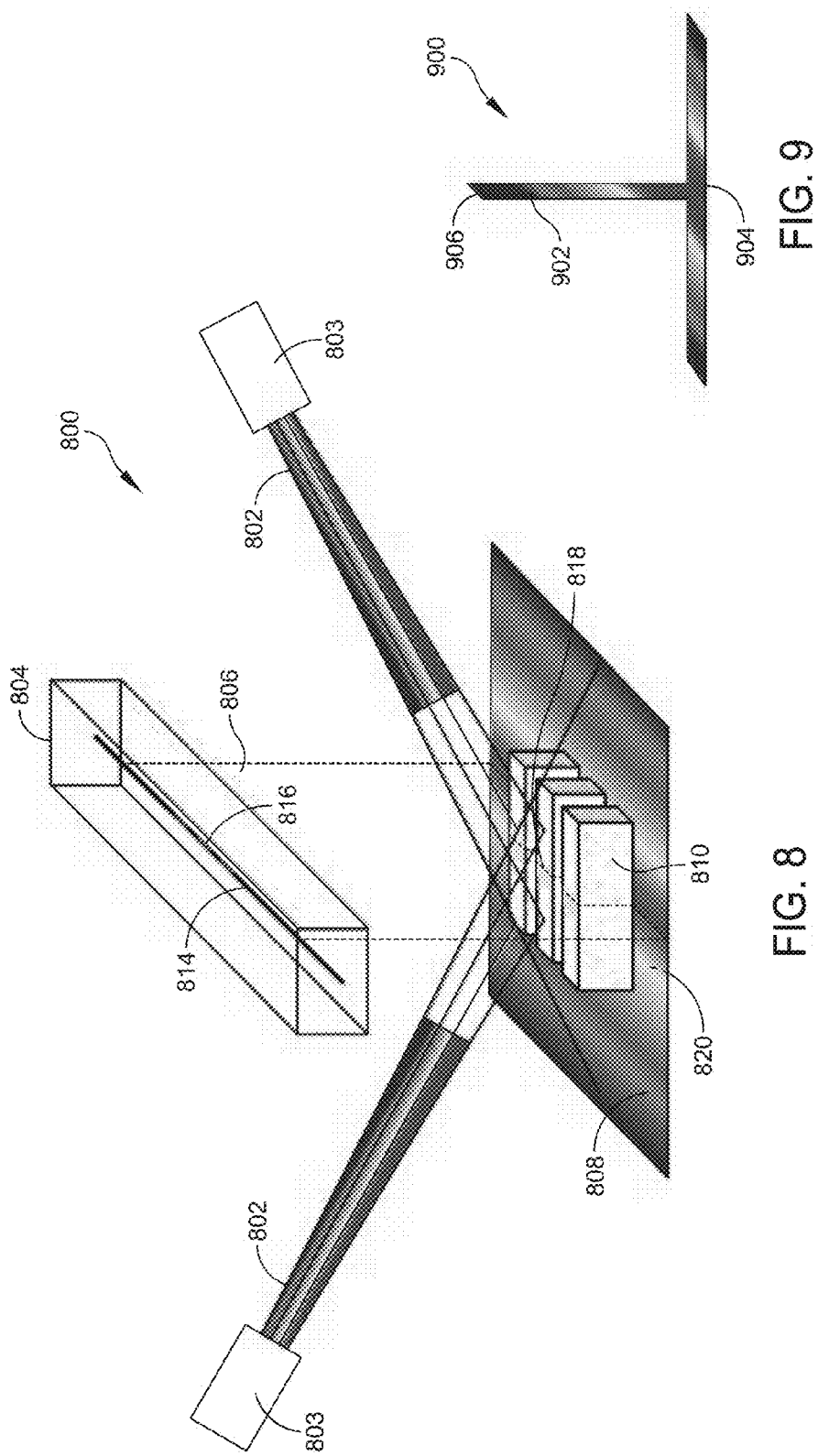

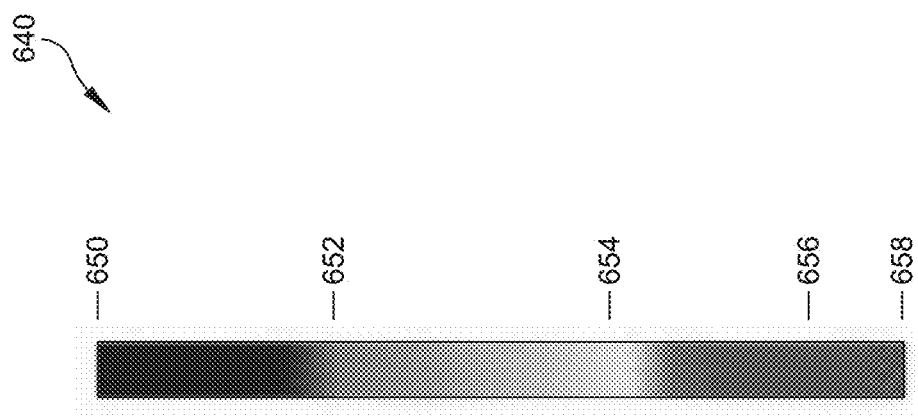

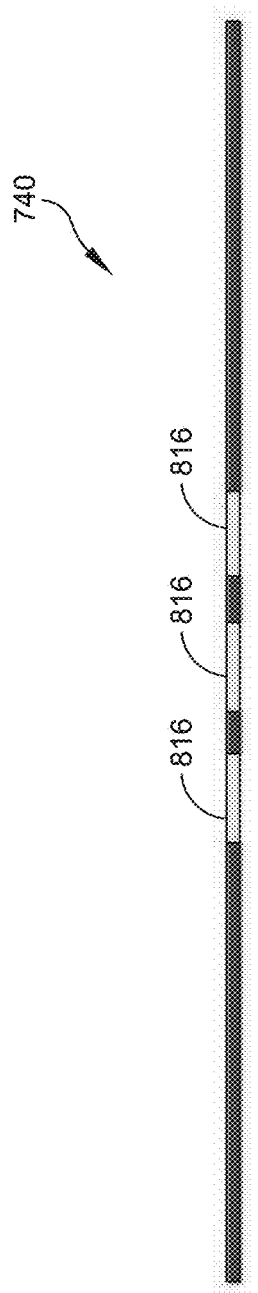

US 8,939,074 B2

COLOR-BASED LINEAR THREE DIMENSIONAL ACQUISITION SYSTEM AND METHOD

BACKGROUND OF THE DISCLOSURE

1. Field of the Disclosure

This disclosure relates generally to systems and methods for depositing a material on a substrate, such as a printed circuit board, and more particularly to an apparatus and systems and methods for inspecting such deposits.

2. Discussion of the Related Art

There are several types of prior art material application systems used for depositing assembly materials, such as solder, for a variety of applications.

One such application uses a stencil printer to print solder paste onto a circuit board. In a typical surface-mount circuit board manufacturing operation, a stencil printer is used to print solder paste or some other material onto the circuit board, which has a pattern of pads or some other conductive surface onto which solder paste will be deposited. The circuit board is automatically fed into the stencil printer and one or more small holes or marks on the circuit board, called fiducials, is used to properly align the circuit board with the stencil or screen of the stencil printer prior to the printing of solder paste onto the circuit board. Once the circuit board has been properly aligned with the stencil in the printer, the circuit board is raised to the stencil, solder paste is dispensed onto the stencil, and a wiper blade (or squeegee) traverses the stencil to force the solder paste through apertures formed in the stencil and onto the board. As the wiper blade is moved across the stencil, the solder paste tends to roll in front of the blade, which desirably causes mixing and shearing of the solder paste so as to attain desired viscosity to facilitate filling of the apertures in the screen or stencil. The solder paste is typically dispensed onto the stencil from a standard cartridge. In other embodiments, a pressurized head may be provided to dispense solder paste to apertures in the stencil.

Another such application in the assembly of integrated circuit chips and other electronic components onto circuit board substrates uses automated dispensing systems for dispensing very small precise amounts, as dots or continuous lines, of viscous material onto a circuit board. The viscous material may include liquid epoxy or solder paste, or some other related assembly material.

In both of the aforementioned systems, it is common that after such material is deposited onto a circuit board, an imaging system is employed to take images of areas of the circuit board for, in certain instances, the purpose of inspecting the accuracy of the deposit of material on the circuit board. Another application of the imaging system involves the aforementioned aligning of the stencil and the circuit board prior to printing in order to register the openings of the stencil with the electronic pads of the circuit board. One such imaging system is disclosed in U.S. Pat. No. 7,458,318 to Prince, which is owned by a subsidiary of the assignee of the present disclosure.

One challenge facing the design of such stencil printers and dispensing systems is the ability to perform a fast, comprehensive inspection of a large area of a substrate after the disposition of solder paste in a single pass. Further, while methods have been developed to perform consistent two-dimensional modeling of solder paste on a substrate, e.g., the circuit board, through existing area-scan and line-scan formats, such approaches are limited various ways. In typical practice, both area-scan and line-scan formats have a limited field of view as a result of the relatively short distance between the lens of the imaging system and the substrate. For example, in area-scan format, imaging a large area may require substantial time as the imaging system moves point-to-point to acquire a large area of a substrate. Likewise, line-scan format may require multiple passes to acquire a large area.

SUMMARY OF THE DISCLOSURE

The disclosure will be more fully understood after a review of the following figures, detailed description and claims.

One aspect of the disclosure is directed to a material applicator. The material applicator comprises a frame and a substrate support coupled to the frame, with the substrate support configured to support an electronic substrate. The material application further comprises a material application device coupled to the frame, with the material application device being configured to deposit assembly material onto the electronic substrate. The material applicator further comprises an imaging system configured to capture three-dimensional image data of the electronic substrate. The imaging system comprises one or more illumination assembly configured to project a spectrum of light substantially along a first axis at an angle to the surface of the electronic substrate. The imaging system further comprises an image sensor assembly configured to detect the spectrum of light reflected from an electronic substrate surface, with the image sensor assembly including a viewing plane. The material application further comprising a controller that is coupled to at least the imaging system, the controller configured to control movement of the imaging system and configured to communicate with the image sensor assembly to produce a three-dimensional image of the topology of the electronic substrate.

Embodiments of the material applicator may include the provision of the one or more illumination assembly including at least one light emitter and a lens configured to concentrate the spectrum of light, which, in certain embodiments, may comprise at least one light emitting diode. The light emitting diode, in certain embodiments, may comprise a phosphor material. The one or more illumination assembly further comprises an optical path adapted to project the spectrum of light between the illumination assembly, the electronic substrate, and the image sensor assembly. Further, the one or more illumination assembly project one or more linear patterns which, in certain embodiments, are projected at opposing angles to strengthen measurable light where the linear patterns intersect along the viewing plane to reduce shadowing effects on the electronic substrate due to adjacent topologies. In some embodiments, the one or more linear patterns may be aligned such that similar colors overlap over a range of elevations along the viewing plane. The light emitter may comprise a prism to split the spectrum of light into component colors, which, in certain embodiments, the spectrum of light is a continuous spectrum of color and arranged in accordance with the HSV color space, or similar color space.

In accordance with another aspect, the disclosure provides an imaging system that is configured to capture three-dimensional image data of solder paste deposited on the electronic substrate within the viewing plane. Further, the three-dimensional image data includes a specific hue that is incident upon surfaces and features along the viewing plane. According to some embodiments, the specific hue corresponds to an elevation.

In accordance with yet another aspect, the disclosure provides a controller which comprises a processor programmed to analyze the three-dimensional image data to determine topology of the electronic substrate and to determine the accuracy of the solder paste deposits on the electronic substrate.

In accordance with another aspect, the disclosure provides a stencil coupled to the frame, the stencil having a plurality of apertures formed therein, and wherein the imaging system is configured to operate between the stencil and the support.

In accordance with yet another aspect, a method of imaging material on a substrate, the method including the acts of: delivering an electronic substrate to a material applicator; performing a dispense operation to deposit assembly material onto the electronic substrate; positioning an imaging system over the electronic substrate; projecting one or more spectrums of light substantially along a first axis at an angle to the surface of the electronic substrate; detecting the one or more spectrums of light reflected from a electronic substrate surface; and capturing three-dimensional image data of a topology of the electronic substrate.

In accordance with another aspect, the method of imaging material on a substrate further comprises the acts of: positioning the electronic substrate in a print position; and positioning a stencil on the electronic substrate. In accordance with yet another aspect, the method of imaging material on a substrate further comprises the act of projecting the one or more spectrums of light in linear patterns. The projecting of one or more spectrums of light in linear patterns comprises projecting the linear patterns at opposing angles to strengthen measurable light where the linear patterns intersect along a viewing plane to reduce shadowing effects on the electronic substrate due to adjacent topologies, which, in certain embodiments the act includes aligning the linear patterns such that similar colors overlap over a range of elevations along the viewing plane. In accordance with yet another aspect, the method of imaging material on a substrate further comprises the act of moving the imaging system from a first position that captures three-dimensional image data of topology of a first area to a second position that captures three-dimensional image data of topology of a second area. According to another embodiment, the method of imaging material on a substrate further comprises splitting the spectrum of light into component colors, wherein, in certain embodiments, further comprising projecting a continuous spectrum of color.

In accordance with yet another aspect of the method of imaging material on a substrate, the method further comprises performing analysis of three-dimensional image data of the at least one area of the electronic substrate to determine accuracy of solder paste deposits on a pad of the electronic substrate. In certain other embodiments, the method of imaging material on a substrate further comprises analyzing the three-dimensional image data for a specific hue incident upon surfaces and features of the electronic substrate, wherein, in certain embodiments further comprising correlating the specific hue with an elevation.

BRIEF DESCRIPTION OF THE DRAWINGS

In the drawings, like reference characters refer to the same or similar parts throughout the different views. The drawings are not necessarily to scale, emphasis instead being placed upon illustrating particular principles, discussed below.

FIG. 5 is a schematic view of an imaging system in a dispenser system according to an embodiment of the disclosure;

FIG. 8 is a diagram representing a projected spectrum from a right and left illuminator at an angle relative to a substrate and intersecting at an optical view plane;

FIG. 9 is cross-sectional view of the optical view plane show in FIG. 8;

FIG. 10 is a diagram representing a color-coded scale corresponding to elevation values of a projected spectrum of FIGS. 8 and 9;

FIG. 11 is a diagram representing a line of image data from a linear color contact image sensor shown in FIG. 8.

DETAILED DESCRIPTION OF THE DISCLOSURE

Figure 1:
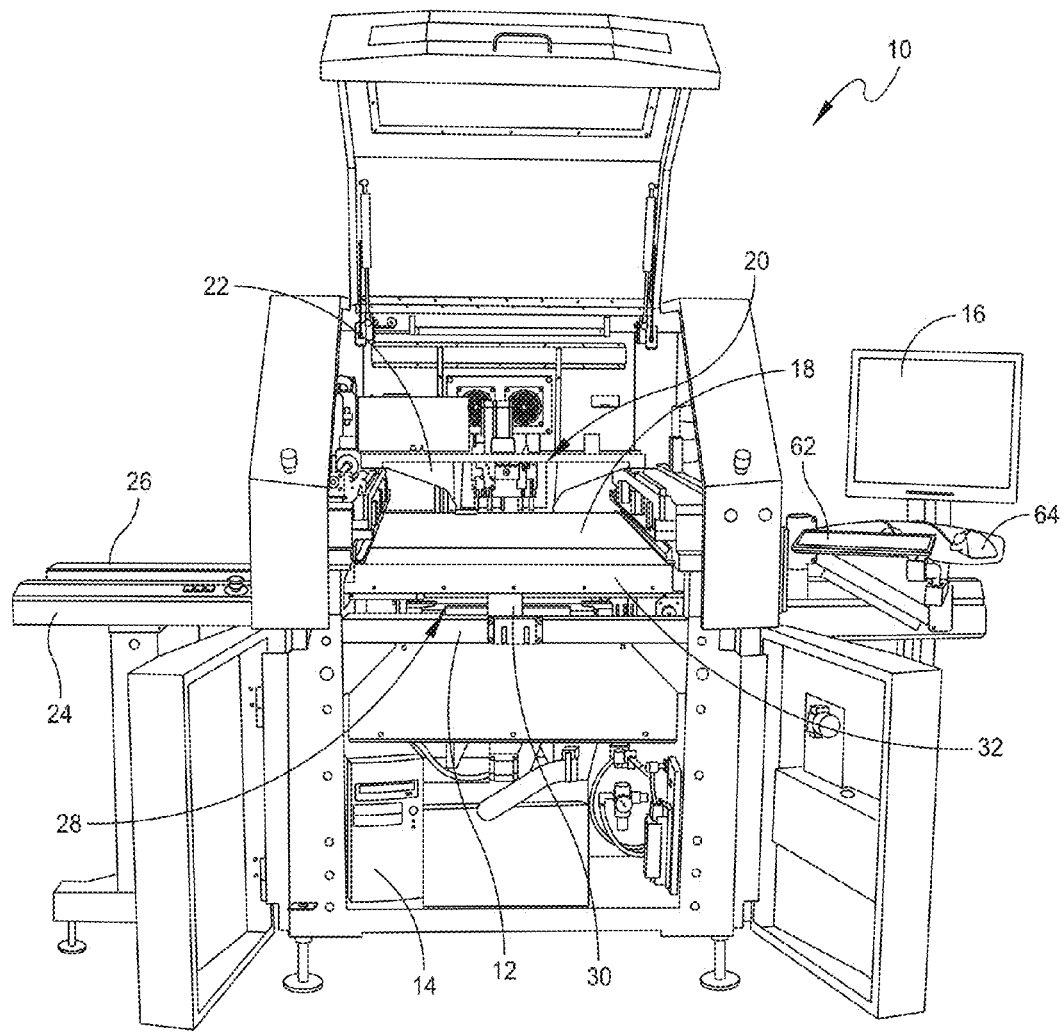
FIG. 1 is a front perspective view of a stencil printer of an embodiment of the present disclosure.

For the purposes of illustration only, and not to limit the generality, the present disclosure will now be described in detail with reference to the accompanying figures. This disclosure is not limited in its application to the details of construction and the arrangement of components set forth in the following description or illustrated in the drawings. The principles set forth in this disclosure are capable of other embodiments and of being practiced or carried out in various ways. Also the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Various embodiments of the present disclosure are directed to material deposition or application systems, devices including such material deposition systems, and methods of depositing material. For purposes of illustration, embodiments of the present disclosure will now be described with reference to a stencil printing systems used to print assembly materials, such as, solder paste onto a circuit board. Further, embodiments of the present disclosure will be described with reference to dispenser systems used to dispense materials, such as semi-viscous and viscous materials, on an electronic substrate, such as a printed circuit board. Such materials include, and are not limited to, solder paste, epoxy, underfill materials, and encapsulants, all of which are used in the fabrication of printed circuit boards. Other less viscous materials, such as conductive inks, may also be used.

One skilled in the art will appreciate that embodiments of the present disclosure are not limited to stencil printers and dispensers that deposit solder paste and other materials onto circuit boards, but rather, may be used in other applications requiring dispensing of other viscous materials, such as glues, encapsulants, underfills, and other assembly materials suitable for attaching electronic components onto a circuit board. Thus, any reference to solder paste herein contemplates use of such other materials. Also, the terms "screen" and "stencil" may be used interchangeably herein to describe a device in a printer that defines a pattern to be printed onto a substrate. In certain embodiments, the stencil printer may include an Accela® or Momentum® series stencil printer platform offered by Speedline Technologies, Inc. of Franklin, Mass.

Referring now to the drawings, and more particularly to FIG. 1, there is generally indicated at 10 a stencil printer of an embodiment of the disclosure. As shown, the stencil printer 10 includes a frame 12 that supports components of the stencil printer. The components of the stencil printer may include, in part, a controller 14, a display 16, a stencil 18, and a print head assembly or print head generally indicated at 20, which is configured to apply the solder paste in a manner described in greater detail below.

As shown in FIG. 1 and described below, the stencil and the print head may be suitably coupled or otherwise connected to the frame 12. In one embodiment, the print head 20 may be mounted on a print head gantry 22, which may be movably mounted on the frame 12. The print head gantry 22 enables the print head 20 to be moved in the y-axis direction under the control of the controller 14 and to apply pressure on the print head as it engages the stencil 18. In one embodiment, the print head 20 may include a pair of squeegee blades that are placed over the stencil 18 and lowered in the z-axis direction into contact with the stencil so that the squeegee blades engage the stencil and create a seal. Once engaged, the squeegee blades of the print head 20 are moved by means of the gantry 22 across the stencil 18 to allow printing of solder paste onto a circuit board through apertures formed in the stencil.

The stencil printer 10 may also include a conveyor system having rails 24, 26 for transporting a printed circuit board (sometimes referred to as a "printed wiring board," "substrate," or "electronic substrate" herein) to a print position in the stencil printer. The rails 24, 26 sometimes may be referred to herein as a "tractor feed mechanism," which is configured to feed, load or otherwise deliver circuit boards to the working area of the stencil printer, which may be referred to herein as a "print nest," and to unload circuit boards from the print nest. The stencil printer 10 has a support assembly 28 to support the circuit board, which raises and secures the circuit board so that it is stable during a print operation. In certain embodiments, the substrate support assembly 28 may further include a particular substrate support system, e.g., a solid support, a plurality of pins or flexible tooling, which is positioned beneath the circuit board when the circuit board is in the print position. The substrate support system may be used, in part, to support the interior regions of the circuit board to prevent flexing or warping of the circuit board during the print operation.

In one embodiment, the print head 20 may be configured to receive solder paste from a source, such as a dispenser, e.g., a solder paste cartridge, that provides solder paste to the print head during the print operation. Other methods of supplying solder paste may be employed in place of the cartridge. For example, solder paste may be manually deposited between the blades or from an external source. Additionally, in a certain embodiment, the controller 14 may be configured to use a personal computer having a suitable operating system, such as a Microsoft Windows® operating system, with application specific software to control the operation of the stencil printer 10. The controller 14 may be networked with a master controller that is used to control a production line for fabricating circuit boards.

In one configuration, the stencil printer 10 operates as follows. A circuit board is loaded into the stencil printer 10 using the conveyor rails 24, 26. The support assembly 28 raises and secures the circuit board to a print position in the print nest. The print head 20 is then lowered in the z-axis direction until the blades of the print head contact the stencil 18 at a desired pressure. The print head 20 is then moved in the y-axis direction across the stencil 18 by the print head gantry 22. The print head 20 deposits solder paste through apertures in the stencil 18 and onto the circuit board. Once the print head has fully traversed the stencil 18 across the apertures, the print head is lifted off the stencil and the circuit board is lowered back onto the conveyor rails 24, 26 with the solder paste deposits left on the circuit board. The circuit board is released and transported from the stencil printer 10 so that a second circuit board may be loaded into the stencil printer. To print on the second circuit board, the print head is lowered in the z-axis direction into contact with the stencil and moved across the stencil 18 in the direction opposite to that used for the first circuit board.

Still referring to FIG. 1, an imaging system generally indicated at 30 may be provided for the purposes of aligning the stencil 18 with the circuit board prior to printing and for inspecting the circuit board after printing. In one embodiment, the imaging system 30 may be disposed between the stencil 18 and the support assembly 28 upon which a circuit board is supported. The imaging system 30 is coupled to an imaging gantry 32 to move the imaging system. In one embodiment, the imaging gantry 32 may be movably coupled to the frame 12, and includes a beam that extends between side rails of the frame 12 to provide back and forth movement of the imaging system 30 over the circuit board in a y-axis direction. The imaging gantry 32 further may include a traveling support bracket, which houses the imaging system 30, and is configured to move along the length of the beam in an x-axis direction. The construction of the imaging gantry 32 used to move the imaging system 30 is well known in the art of solder paste printing. The arrangement is such that the imaging system 30 may be located at any position below the stencil 18 and above the circuit board to capture an image of predefined areas of the stencil or circuit board, respectively. In other embodiments, when positioning the imaging system outside the print position the imaging system may be located above or below the stencil and the circuit board.

Figure 2:
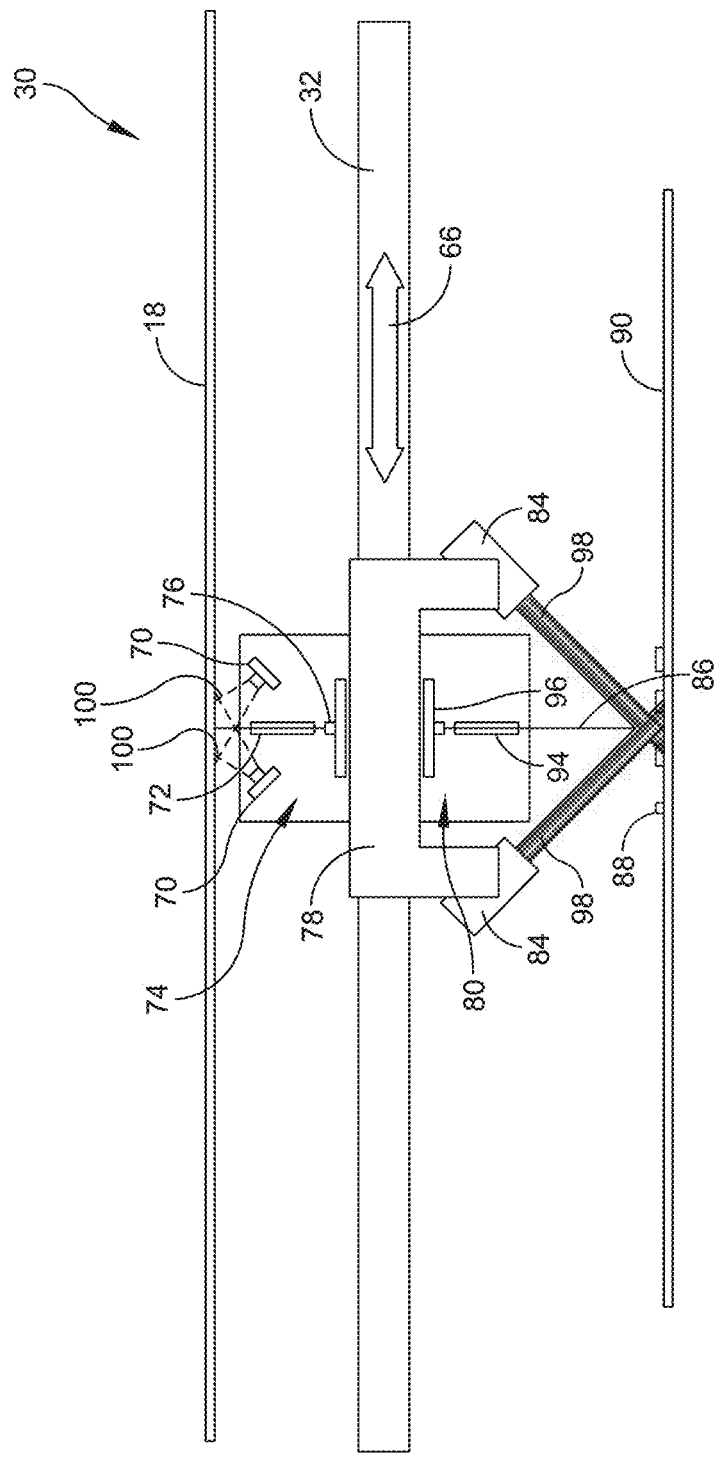
FIG. 2 is a schematic view of an imaging system in a screen printer according to an embodiment of the disclosure.

Referring to FIG. 2 in addition to FIG. 1, the imaging system 30 is disposed between the stencil 18 and the circuit board 90, which in turn is supported by the support assembly, such as the support assembly 28. The imaging system 30 is coupled to a gantry system 32 (FIG. 1), which may be part of the gantry used to move the print head 20 or provided separately within the stencil printer 10. The construction of the gantry system 32 used to move the imaging system 30 is well known in the art of stencil printing. The arrangement is such that the imaging system 30 may be located at any position along a scan axis 66 below the stencil 18 and above the circuit board 90 to determine topology of predefined areas of the circuit board or stencil, respectively. In other embodiments, when positioning the imaging system 30 outside the printing nest, the imaging system 30 may be located above or below the stencil 18 and the circuit board 90.

As shown in FIG. 2, in one embodiment, the imaging system 30 includes a contact image sensor (CIS) assembly generally indicated at 74, to image the stencil, such as stencil 18. The CIS assembly 74 has a CIS rod-lens array 72, right and left CIS LED illuminators each indicated at 70, and a CIS pixel array 76. In certain embodiments, the CIS pixel array 76, a rod-lens array 72 and the right and left illuminators 70 may be configured together as an integrated imaging assembly. Such an assembly, as well as the imaging system 30, may also be referred to as CIS assembly with integral LED illumination. The right and left CIS LED illuminators 70 may be identical in construction with respect to one another. Each of the right and left CIS LED illuminators 70 may include an LED array, prism, and focusing optics, and be configured to project a spectrum of light 100 on to the stencil 18 at a relative angle. In the shown embodiment, the CIS pixel array 76 is of the monochrome variety, whereby only brightness values are available to create a gray scale image of the stencil 18. In yet another embodiment, the CIS pixel array 76 and right and left CIS LED illuminators 70 may be configured identically to CIS pixel array 96 and external right and left CIS LED illuminators 84, respectively. Such a configuration would enable the CIS pixel array 76 to detect a range of hues incident to the surface of the stencil 18, and thus, determine topographical features of stencil 18. In certain embodiments, the spectrum of light 100 may be projected at opposing angles. Alternatively, a single CIS LED illuminator may be used to project the spectrum of light 100 on to the stencil 18.

Still referring to FIG. 2, in one embodiment, the imaging system 30 further includes a CIS assembly generally indicated at 80 to image the substrate. The CIS assembly 80 has a CIS rod-lens array 94, a CIS pixel array 96, and external right and left CIS LED illuminators each indicated at 84. In certain embodiments, the pixel array 96 and the rod-lens array 94 may also be referred to as a CIS assembly with external LED illuminators. The right and left CIS LED illuminators 84 may each include an LED array, prism, and focusing optics and be configured to project a spectrum of light 98 at an angle relative to the circuit board 90. In certain embodiments, the spectrum of light 98 may be projected at opposing angles. Alternatively, a single CIS LED illuminator may be used to project the spectrum of light 98 on to the circuit board 90. The CIS pixel array 96 and the CIS rod-lens array 94 may be configured to determine topographical features 88 provided on the circuit board 90 based on detecting a specific hue incident upon the surface of the circuit board 90 within an optical view plane 86, which will be described in greater detail below.

Figure 3:
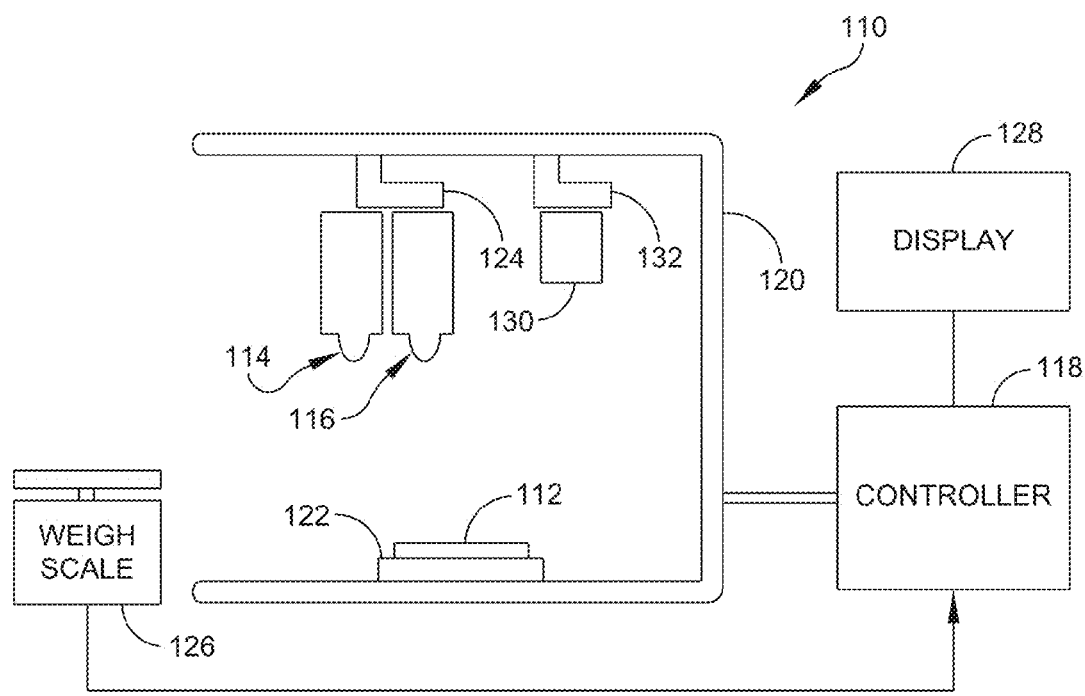
FIG. 3 is a side schematic view of a material deposition or application system.

FIG. 3 schematically illustrates a dispenser, generally indicated at 110, according to one embodiment of the present disclosure. The dispenser 110 is used to dispense a viscous material (e.g., an adhesive, encapsulant, epoxy, solder paste, underfill material, etc.) or a semi-viscous material (e.g., soldering flux, etc.) onto an electronic substrate 112, such as a printed circuit board or semiconductor wafer. The dispenser 110 may alternatively be used in other applications, such as for applying automotive gasketing material or in certain medical applications. As described above, it should be understood that references to viscous or semi-viscous materials, as used herein, are exemplary and intended to be non-limiting. The dispenser 110 includes first and second dispensing units or heads, generally indicated at 114 and 116, respectively, and a controller 118 to control the operation of the dispenser. Although two dispensing units are shown, it should be understood that one or more dispensing units may be provided.

The dispenser 110 may also include a frame 120 having a base or support 122 for supporting the substrate 112, a dispensing unit gantry 124 movably coupled to the frame 120 for supporting and moving the dispensing units 114, 116, and a weight measurement device or weigh scale 126 for weighing dispensed quantities of the viscous material, for example, as part of a calibration procedure, and providing weight data to the controller 118. A conveyor system (not shown) or other transfer mechanism, such as a walking beam, may be used in the dispenser 110 to control loading and unloading of substrates to and from the dispenser. The gantry 124 can be moved using motors under the control of the controller 118 to position the dispensing units 114, 116 at predetermined locations over the substrate. The dispenser 110 may include a display unit 128 connected to the controller 118 for displaying various information to an operator. There may be an optional second controller for controlling the dispensing units.

Prior to performing a dispensing operation, as described above, the substrate, e.g., a printed circuit board, must be aligned or otherwise in registration with a dispenser of the dispensing system. The dispenser further includes a vision system 130, which is coupled to a vision system gantry 132 movably coupled to the frame 120 for supporting and moving the vision system. Although shown separately from the dispensing unit gantry 124, the vision system gantry 132 may utilize the same gantry system 124 as the dispensing units 114, 116. As described, the vision system 130 is employed to verify the location of landmarks, known as fiducials or other features and components, on the substrate. Once located, the controller 118 can be programmed to manipulate the movement of one or both of the dispensing units 114, 116 to dispense material on the electronic substrate.

Systems and methods of the present disclosure are directed to determining topographical features of the substrate 112. The description of the systems and methods provided herein reference exemplary electronic substrates (e.g., printed circuit boards), which are supported on the support 122 of the dispenser 110. In one embodiment, the dispense operation is controlled by the controller 118, which may include a computer system configured to control material dispensers. In another embodiment, the controller 118 may be manipulated by an operator.

Figure 4:
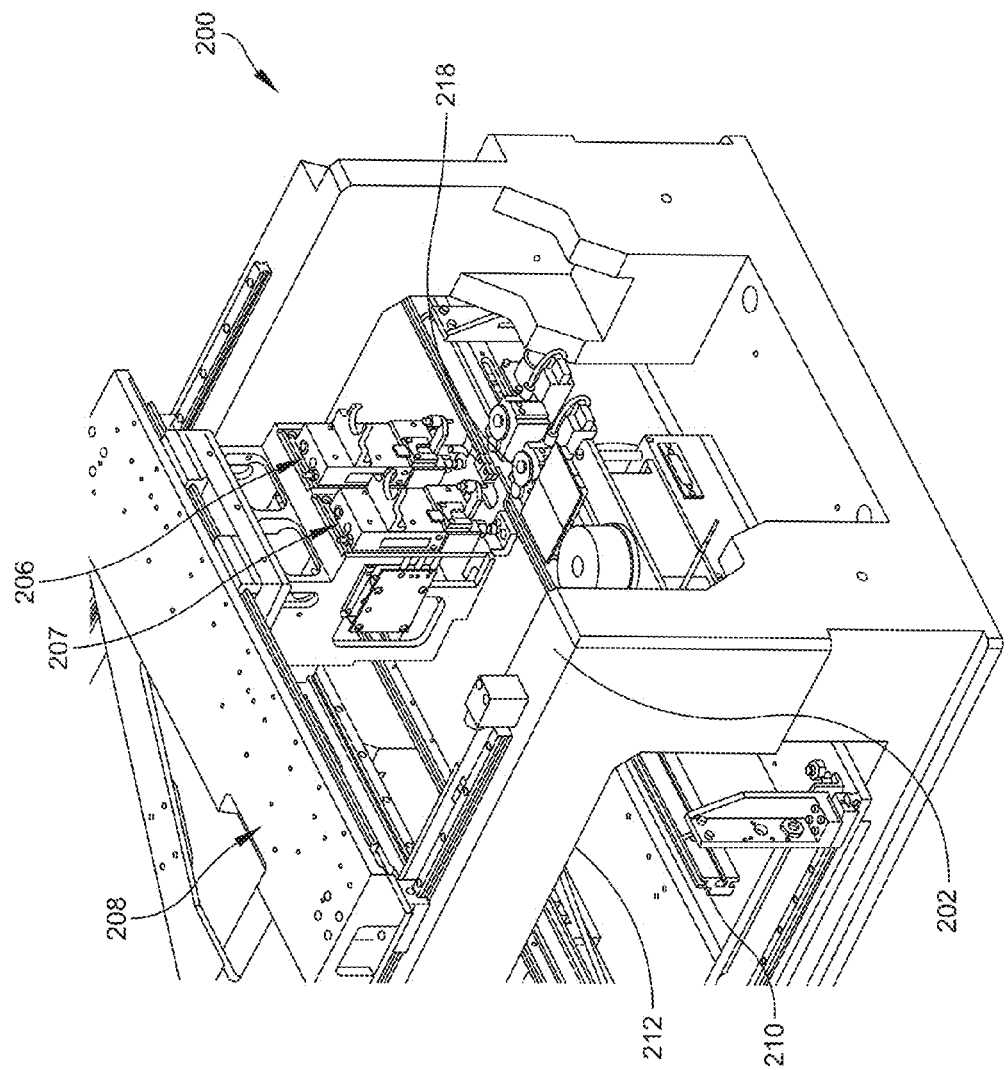
FIG. 4 is a partial perspective view of an exemplary material deposition system embodying a gantry system, two material deposition heads and other components of an embodiment of the present disclosure.

Referring to FIG. 4, an exemplary material deposition system or dispenser, generally indicated at 200, may be configured from a XYFLEXPRO® or a FX-D® dispenser platform offered by Speedline Technologies, Inc. of Franklin, Mass. In one embodiment, the material deposition system 200 includes a frame 202 that supports components of the material deposition system, including but not limited to a controller, such as the controller 118 shown in FIG. 3, which is located in a cabinet of the material deposition system, and two deposition or dispensing heads, generally indicated at 206 and 207, for depositing low viscous materials (e.g., less than 50 centipoise), semi-viscous materials (e.g., 50-100 centipoise), viscous materials (e.g., 100-1000 centipoise), and/or high viscous materials (e.g., greater than 1000 centipoise). The deposition heads 206, 207 may be movable along orthogonal axes by a gantry system, generally indicated at 208, under the control of the controller 118 to allow dispensing of the material on the circuit board, such as substrate 112 shown in FIG. 3, which, as mentioned above, may sometimes be referred to as an electronic substrate or a circuit board. A cover (not shown) may be provided but is not shown so as to reveal the internal components of the material deposition system 200, including the deposition heads 206, 207 and the gantry system 208. Although two deposition heads 206, 207 are shown and described, any number of deposition heads may be provided and fall within the scope of the present disclosure.

Circuit boards, such as substrates 112, which are fed into the material deposition system 200, typically have a pattern of pads or other surface areas onto which material will be deposited. The material deposition system 200 also includes a conveyor system 210 that is accessible through an opening 212 provided along each side of the material deposition system to transport the circuit board in an x-axis direction to a depositing position in the material deposition system. When directed by the controller of the material deposition system 200, the conveyor system 210 supplies circuit boards to a dispense location under the deposition heads 206, 207. Once arriving at the position under the deposition heads 206, 207, the circuit board is in place for a manufacturing operation, e.g., a deposition operation.

As mentioned above, the material deposition system 200 further includes a vision inspection system, such as the vision inspection system 130 shown in FIG. 3, that is configured to align the circuit board and to and inspect the material deposited on the circuit board. In one embodiment, the vision inspection system 130 is secured to one of the deposition heads 206, 207 or to the gantry system 208. To successfully deposit material on the circuit board, the circuit board and the deposition heads 206, 207 are aligned, via the controller 118. Alignment is accomplished by moving the deposition heads 206, 207 and/or the circuit board based on readings from the vision inspection system. When the deposition heads 206, 207 and the circuit board are aligned correctly, the deposition heads are manipulated to perform a deposition operation. After the deposition operation, optional inspection of the circuit board by means of the vision inspection system may be performed to ensure that the proper amount of material has been deposited and that the material has been deposited at the proper locations on the circuit board. The vision inspection system may use fiducials, chips, board apertures, chip edges, or other recognizable patterns on the circuit board to determine proper alignment. After inspection of the circuit board, the controller controls movement of the circuit board to the next location using the conveyor system, where a next operation in the board assembly process may be performed, for example electrical components may be placed on the circuit board or the materials deposited on the board may be cured.

In some embodiments, the material deposition system 200 may operate as follows. The circuit board may be loaded into the material deposition system 200 in a depositing position using the conveyor system 210. The circuit board is aligned with the deposition heads 206, 207 by using the vision inspection system. The deposition heads 206, 207 may then be initiated by the controller 118 to perform a deposit operation in which material is deposited at precise locations on the circuit board. Once the deposition heads 206, 207 have performed a depositing operation, the circuit board may be transported by the conveyor system from the material deposition system 200 so that a second, subsequent circuit board may be loaded into the material deposition system.

Referring to FIG. 5, an imaging system of an embodiment of the present disclosure is generally designated at 500, which is substantially the same as the imaging system 30 shown in FIG. 2 except without, for example, the CIS assembly 74 to image the stencil. Otherwise, the imaging system 500 may be configured identically to the imaging system 30 of FIG. 2. As such, the CIS assembly 80 may be coupled to a traveling support bracket 78, which is in turn movably coupled to the gantry system 132. As described above, a CIS assembly with external illuminators or a CIS assembly with integral illumination may be included in the vision inspection system 130 of FIG. 3. To this end, the CIS assembly may be configured to determine topographical features 88 provided on the circuit board 90 based on detecting a specific hue incident upon the surface of the circuit board 90 within an optical view plane 86, which will be described in greater detail below.

As shown schematically, in reference to FIG. 5, the CIS assembly 80 includes a rod-lens array 94 configured to function telecentrically, and a linear pixel array 96. The collective CIS assembly 80 may be referred to as "CIS optics." In other embodiments, the CIS assembly 80 may be replaced by a Line-Scan camera. It is important to note that CIS and Line-Scan cameras typically have a single "line of view" versus a typical Area-Scan camera that captures a two dimensional "field of view." Further, area-scan camera systems have a three-dimensional (volumetric) optical path between the lens and the two dimensional "field of a view," while a CIS or line-scan camera only has a two-dimensional "optical plane" between the lens which creates a single "line of view" where objects intercept the optical plane. To this end, the term "line of view" more accurately describes a one-dimensional region of interest, as acquired by a CIS or line-scan camera, than would the term "field of view," which would imply a two-dimensional area. Therefore, the term "optical plane" used herein describes the optical path that rays of light follow from the "line of view" to the lens.

CIS optics may be configured in multiple ways. A few common configurations will now be discussed. The following configurations are examples and are intended to be non-limiting. In one embodiment, a tri-linear color CIS may be used. This embodiment may include a lens or prism to the rod-lens array to allow a common focal point for corresponding red, green, and blue pixels along the line of view. Accordingly, subsequent processing of red, green, and blue pixel values would produce accurate hue and a corresponding elevation value.

As mentioned above, typical CIS optics consists of an array of gradient rod lenses that are inherently telecentric and compact. For a tri-linear color CIS with a typical rod-lens array, the displacement of red, green and blue rows of pixels causes each row to capture a different line of view, and, thus, receive a different hue due to corresponding lateral displacement of the projected color pattern. Regardless of this offset, subsequent processing of red, green and blue pixel values may produce a unique hue and a corresponding elevation value of the surface of the substrate. Resolution along the line of view would correspond to nominal pixel spacing with no interpolation required.

In yet another embodiment, a color CIS configured to have a single row of repeating red, green and blue pixel values may enable a common line of view. Accordingly, subsequent processing of red, green, and blue pixel values would produce accurate hue and a corresponding elevation value of the surface of the substrate. However, resolution along the line of view may be slightly reduced due to progressive grouping of color pixels, in this example, three per group, and may require subsequent interpolation similar to Bayer pattern conversion.

In still another embodiment, a color CIS configured to have a single row of Foveon pixels, each consisting of three vertically stacked photodiodes, may have a common line of view and may collectively operate as a Foveon direct image sensor. It should be understood that Foveon direct image sensors, described in the aforementioned configuration, are unlike traditional image sensors. It should be understood that prior to the availability of Foveon direct image sensors, there was a 1:1 relationship between the number of pixels (photodetectors) and the number of pixel locations for a traditional CCD and CMOS image sensor. Given this relationship, the generic term "pixel" has been commonly used in the art to reference both the pixel (photodetector) and the pixel location. Foveon direct image sensors are a new type of image sensor that incorporates three pixels (photodetectors) at every pixel location on the image sensor. Thus, the definition of a pixel as used herein may include traditional CCD image sensors, CMOS image sensors, and the Foveon direct image sensors. Accordingly, the subsequent processing of red, green, and blue pixel values may produce an accurate hue and a corresponding elevation value of the surface of the substrate. Resolution along the line of view may correspond to nominal pixel spacing with no interpolation required.

In one embodiment, the CIS LED illuminators 84 may include one or more light emitting diodes (white light diodes), arranged in an array, that are capable of generating an intense amount of light, a prism to split the white light into a continuous spectrum of component colors, and focusing optics to concentrate the projected colors into a pattern wherein height measurements are possible across the full width of the CIS optics. LEDs may also be staggered, nested, and/or "piped" as required to facilitate packaging or to adjust geometry and uniformity of the projected color patterns.

Figure 7:
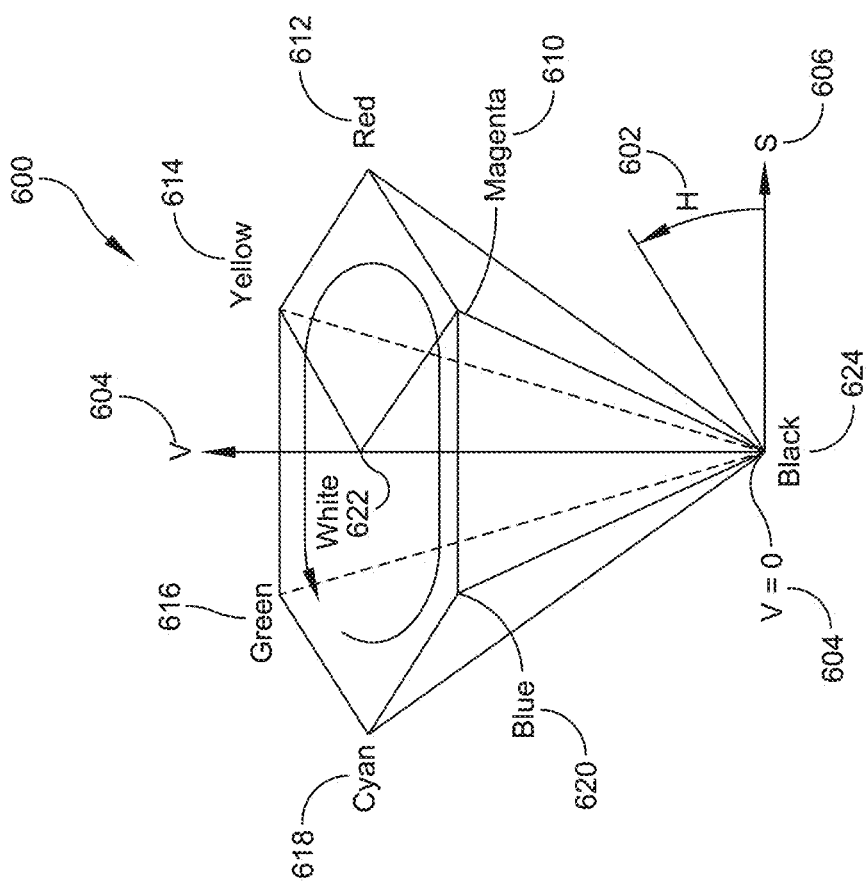
FIG. 7 a diagram of an HSV hexagonal cylinder depicting the independently measurable hues of the HSV color space according to one embodiment of the disclosure.
Figure 6:
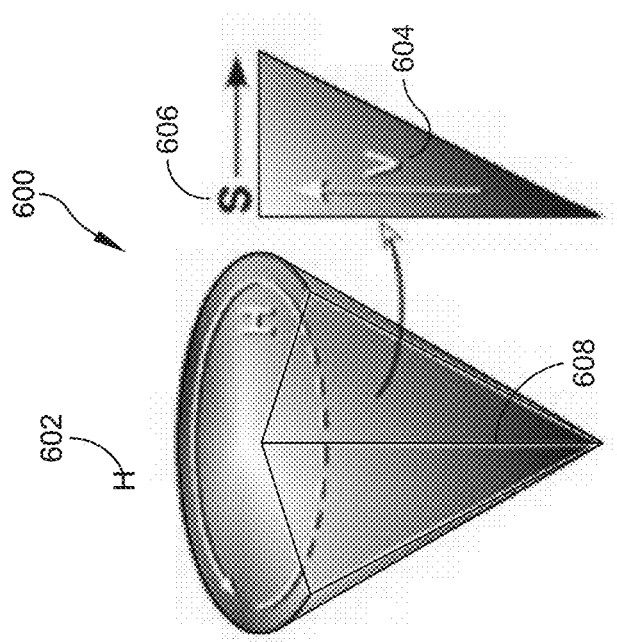
FIG. 6 is a diagram depicting the HSV color classification system defined by hue, saturation and value (brightness) characteristics.

The projected spectrum of component colors may be one of numerous color spaces, which allows a dominant color (hue) to be measured independently of color purity (saturation) and relative brightness (value). FIGS. 6 and 7 depict one such color space, which may be referred to as HSV (hue, saturation, value). In FIG. 6, an angle around a central vertical axis 608 of a cone 600 corresponds to a hue 602. The distance from the central vertical axis 608 to a specific hue 602 corresponds to a saturation 606. The distance along the vertical axis 608 corresponds to "lightness" or value 604.

FIG. 7 illustrates a HSV hexagonal cylinder depicting independently measureable (dominant) hues of the HSV color space according to one embodiment. The CIS LED illuminators 84 may project one or more of the colors including magenta 610, red 612, yellow 614, green 616, cyan 618 and blue 620. The CIS LED illuminators may be configured to project a pattern of non-repeating hues corresponding to measurable values of the HSV cylinder 600 which may be translated into a value between 0° and 360°, or any appropriate unit such as, 0-255 (8-bit), 0-1024 (10-bit), etc. The listed unit translations are not meant to be limiting, and it should be apparent that the values may be translated into a unit which is most practical or convenient for subsequent handling, processing, storage, or to achieve a desired resolution. For example, 8-bit provides 256 divisions and enables efficient and compact storage in memory. Further, this would provide 3.9 um graduations over a 1 mm distance (1000 um/256=3.9 um), which may be an appropriate range and resolution for some applications. Still other applications may require more resolution, and thus, more bits to facilitate smaller (finer) divisions.

In one exemplary embodiment, the CIS LED illuminators project a color pattern that is unique and progresses continuously through the working spectrum. This continuous progression of color prevents a shift in apparent hue that may occur when the natural reflectance of an object favors a particular wavelength. In HSV color space, hue is independent of saturation and relative value or "brightness." In such an embodiment, only one hue is incident upon an object at any specific elevation along the line of view. The hue may be accurately detected regardless of the reflective efficiency, or relative brightness of the given object at a given location, at that wavelength.

Referring to FIG. 8, in one embodiment, an imaging system assembly, generally indicated at 800, consists of one or more projected patterns of light, which represents a range of height measurements along a full working width of a CIS or Line-Scan camera. In the shown embodiment, the imaging system 800 consists of a right and left pattern of projected colors, each indicated at 802, projected from one or more CIS LED illuminators, each indicated at 803. A substrate 808, with a component or supplied feature 810, such as solder paste, is supported by a substrate support 820 and positioned bellow a CIS assembly 804, which in turn houses an image sensor comprising a linear array of light sensing pixels 814. The image sensor 814 consists of a single row of repeating red, green, and blue (RGB) sensitive pixels which, together with the rod-lens array 94 (FIG. 5) have a common line of view over the full width of an optical plane 806. To this end, the right and left pattern of projected colors 802 incident to the component surface 818 travel through the optical plane 806 to the rod-lens array 94 (FIG. 5), and arrive at the linear pixel array 814. This enables the detection of dominant hue at location 816 along the pixel array. The corresponding elevation value of the substrate component surface 818 will be further discussed below, with reference to FIGS. 9 and 10.

In one embodiment, shown in FIG. 11, one line of color image data from the image sensor 814 (FIG. 8) is represented. In this embodiment, the dominant hue incident to the component 818 (FIG. 8) is detected by image sensor 814 (FIG. 8) at location 816 (FIG. 11). The width and resolution of the CIS optics is based on the arrangement of the red, green and blue rows of pixels within the image sensor 814 (FIG. 8). Design of the LED array, prism and focusing optics of the CIS optics may be modified as required to set working distance, concentration, and dimension of a spectral pattern to enable a specific range of height measurement along the full working width of a CIS camera. Design of the rod-lens array 94 (FIG. 5) may also be modified as required to set a working distance, thus providing the required clearance for the projected patterns of light 802 (FIG. 8).

Returning to FIG. 8, the imaging system 800 includes at least two LED illuminators 803 that project, at an angle relative to the optical plane, a spectrum of color focused so that a specific range of height measurements may be determined by the detection of a hue incident upon the surface of a substrate. The benefit of such a configuration is that the two or more CIS LED illuminators are projecting a spectrum of color at opposing angles, which strengthens the measurable signal where they intersect along the optical plane and further reduce any shadowing effects on surfaces along the line of view due to adjacent topography. The opposing spectrums of color overlap over a range of elevations along the viewing plane. To this end, the mixing of colors maintains purity of the projected hue and minimizes any shift in detected hue due to reflective bias (native color) of the illuminated surface.

As shown in FIG. 9, with additional reference to FIG. 8, a one-dimensional cross-section of the projected colors 802 (FIG. 8) from both illuminators 803 along a vertical optical pane is generally indicated at 900. At a bottom of the vertical optical plane 806 is a projected base hue 904 and a maximum hue value 906. In one embodiment, the projected colors would be arranged with regard to the HSV color system and would be progressively and appropriately ordered. For example, the base color 904 would correspond to the value of a red hue and the maximum hue value would be the value of a blue hue. Accordingly, the projected colors would be in a vertical pattern 902 between the base hue value 904 and the maximum hue value 906 and would transition smoothly and continuously from red, to yellow, to green, to cyan, and finally to blue, in this example.

Now referring to FIG. 10, in addition to FIGS. 8 and 9, a scale of corresponding color coded elevations is generally indicated at 640. In the shown embodiment, the scale 640 is based on the HSV color system and consists of progressive colors patterned vertically. According to the shown embodiment, hues corresponding to a minimum and maximum scale is designated as 658 and 650, respectively. In the shown embodiment, a baseline hue 656 may be projected in a repeated pattern to account for an offset in elevation from the substrate 808 to the substrate support 820. To this end, hues above the baseline hue 656, designated as 654, 652 and 650, may correspond directly to an elevation value. For example, hues arriving at image sensor 814 (FIG. 8) that are predominately red may be subsequently located at 656 on the scale in FIG. 10. Accordingly, the detected hue is representative of the working baseline, and indicates that only bare substrate 808 (FIG. 8) is present at corresponding locations along the line of view. Likewise, a dominant hue that is above the baseline hue 656 may indicate the presence of elevated features. For example, if yellow is the dominant hue at 818 (FIG. 8), and that particular hue is detected by the image sensor 816 (FIG. 8), this may indicate elevated topology. The difference, or change in hue between the baseline hue 656 and hue 654, is due to topology of the substrate 808. This change, after conversion to engineering units, corresponds to the relative elevation of such topology above the baseline.

In one alternative embodiment, a "brightness" or value 604 shown in FIG. 6 may be measured in certain embodiments. Returning to FIG. 2, the left and right LED illuminators 70 may be configured to project a monochrome hue 100 at an angle relative to the stencil 18. According to one embodiment, the "brightness" value 604 may be used independently by the controller (e.g., controller 14 shown in FIG. 1) for the purpose of identifying, aligning, or inspecting objects before or after a print or dispense operation.

Figure 12:
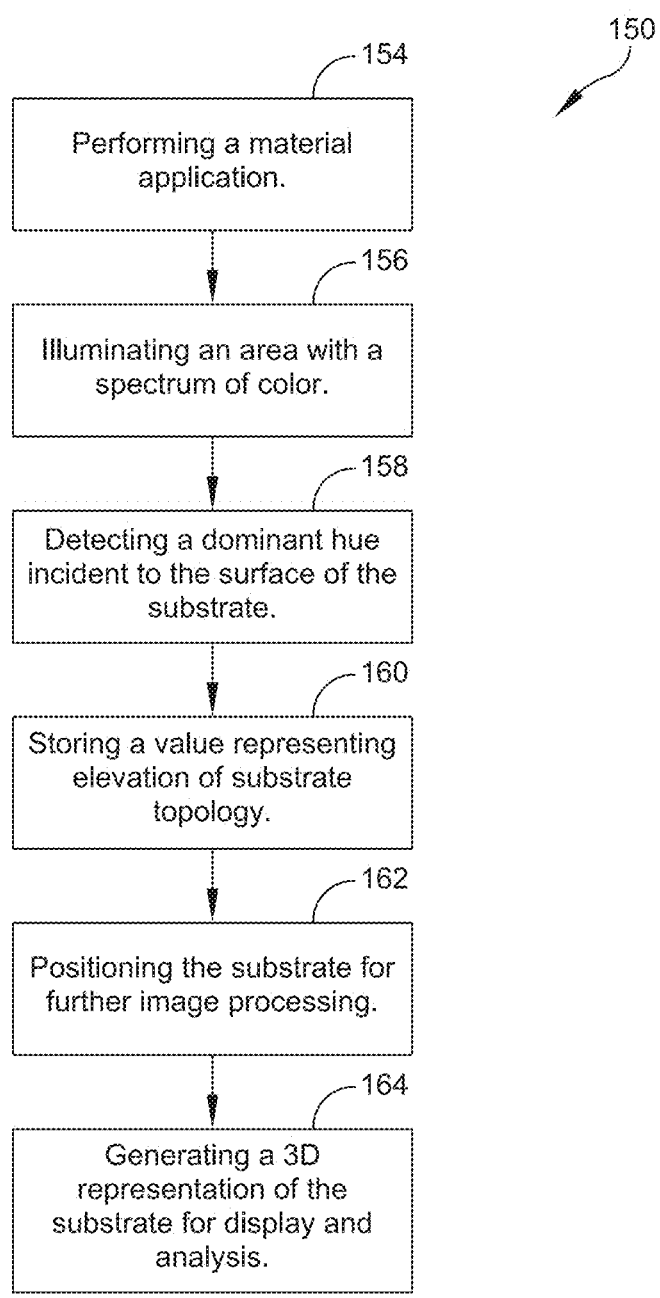
FIG. 12 is a method for dispensing solder paste onto electronics pads of a circuit board according to one embodiment of the disclosure.

Turning now to FIG. 12, a method for dispensing solder paste onto electronics pads of a circuit board is generally designated at 150. As shown, at 154, a material application operation is performed. In one embodiment, a printed circuit board is delivered to a stencil printer via a conveyor system, for example to perform a print operation. With reference to FIG. 1, a circuit board is delivered to the print nest via conveyor rails. Once delivered, the circuit board is positioned within a print nest on top of the support assembly and is then precisely aligned with the stencil using the imaging system, and raised by the support assembly so that it is maintained in a print position. Next, the dispensing head is lowered to engage the stencil to deposit solder paste on to the circuit board. Once printing is completed, inspection of the circuit board and/or stencil may take place. Stencil inspecting may also be performed independently and concurrently as circuit boards are transported to and from the print nest area.

Next, an area of the circuit board is brought into the line of view of the CIS optics. The circuit board (or stencil) is imaged by illuminating the line of view with a spectrum of color at 156. The spectrum of color may be projected at opposing angles. Once the circuit board (or stencil) is adequately illuminated, the CIS optics may detect one or more hues incident to the surface of the circuit board (or stencil) over the full width of the telecentric lens at 158. The detected unique hues correspond to elevations of the circuit board (or stencil). The hues are then converted to a scalar value representing height and stored by the controller.

Next, a subsequent area of the circuit broad or the stencil is imaged. The imaging of the full length of the circuit board is executed by moving the circuit board relative to one pixel, or any number of pixels depending on the desired resolution at 162. Under the direction of the controller, the imaging system sequentially moves the circuit board along the x-axis to detect hues incident to the surface of the circuit board for inspection purposes, for example. In other embodiments, the method 150 may include capturing hues incident to the surface of the stencil instead of or in addition to capturing hues incident to the surface of the circuit board.

Once the circuit board has been processed and series of hue values incident to the surface of the circuit board is stored at 160, a 3D representation of the circuit board may be displayed to a user at 164. In other embodiments, the 3D representation may further be processed by the controller and used to perform analysis of the circuit board.

In one embodiment, the vision system 30 (FIG. 1) may be used to perform a texture recognition method, such as the method disclosed in U.S. Pat. No. 6,738,505 to Prince, entitled METHOD AND APPARATUS FOR DETECTING SOLDER PAST DEPOSITS ON SUBSTRATES, which is owned by a subsidiary the assignee of the present disclosure and incorporated herein by reference. U.S. Pat. No. 6,891,967 to Prince, entitled SYSTEMS AND METHODS FOR DETECTING DEFECTS IN PRINTED SOLDER PASTE, which is also owned by the subsidiary of the assignee of the present disclosure and incorporated herein by reference, furthers the teachings of U.S. Pat. No. 6,738,505. Specifically, these patents teach texture recognition methods for determining whether solder paste is properly deposited onto predetermined regions, e.g., copper contact pads, located on a printed circuit boards.

According to various embodiments of the present disclosure, several advantages may be realized. For example, the disclosed apparatus and methods are capable of performing a fast, 100% inspection of the surface of a substrate. This inspection may include generating a 3-D representation of the substrate using one dimensional technology. Another advantage is the compact nature of the CIS assembly and LED illuminators, which enables placement within systems with limited space for inspection hardware. However, it should be understood that aspects of the various embodiments of the present disclosure may also be included in a standalone inspection system. Further advantages may be realized.

While this disclosure has been shown and described with references to particular embodiments thereof, those skilled in the art will understand that various changes in form and details may be made therein without departing from the scope of the disclosure, which is limited only to the following claims.

What is claimed is:
1. A material applicator comprising:
a frame:
a substrate support coupled to the frame, the substrate support configured to support an electronic substrate;
a material application device coupled to the frame, the material application device being configured to deposit assembly material onto the electronic substrate;
an imaging system configured to capture three-dimensional image data of the electronic substrate, the imaging system comprising
one or more illumination assembly configured to project a spectrum of substantially along a first axis at an angle to the surface of the electronic substrate, and
an image sensor assembly configured to detect the spectrum of light reflected from an electronic substrate surface, the image sensor assembly including a viewing plane; and
a controller coupled to at least the imaging system, the controller configured to control movement of the imaging system and configured to communicate with the image sensor assembly to produce a three-dimensional image of the topology of the electronic substrate,
wherein the imagining system is configured to capture three-dimensional image data of solder paste deposited on the electronic substrate within the viewing plane,
wherein the three-dimensional image data includes a specific hue that incident upon surfaces and features along the viewing plane,
wherein the specific hue corresponds to an elevation,
wherein the one or more illumination assembly projects one or more linear patterns, wherein the one or more linear patterns are projected at opposing angles to strengthen measurable light where the linear patterns intersect along the viewing plane to reduce shadowing effects on the electronic substrate due to adjacent topologies, and wherein the one or more linear patterns are aligned such that similar colors overlap over a range of elevations along the viewing plane.

2. The material applicator of claim 1, wherein one of the one or more illumination assembly includes at least one light emitter and a lens configured to concentrate the spectrum of light, and an optical path adapted to project the spectrum of light between the illumination assembly, the electronic substrate, and the image sensor assembly.

3. The material applicator of claim 2, wherein the light emitter includes a prism to split the spectrum of light into component colors.

4. The material applicator of claim 3, wherein the spectrum of light arranged in accordance with HSV color space, or similar color space.

5. The material applicator of claim 2, wherein the light emitter includes at least one light emitting diode.

6. The material applicator of claim 5, wherein the at least one light emitting diode includes a phosphor material.

7. The material applicator of claim 6, wherein the spectrum of light is a continuous spectrum of color.

8. The material applicator of claim 1, wherein the controller comprises a processor programmed to analyze the three-dimensional image data to determine topology of the electronic substrate to determine the accuracy of the solder paste deposits on the electronic substrate.

9. The material applicator of claim 1, further comprising a stencil coupled to the frame, the stencil having a plurality of apertures formed therein, and wherein the imaging system is configured to operate between the stencil and the support.

* * * * *

UNITED STATES PATENT AND TRADEMARK OFFICE
CERTIFICATE OF CORRECTION

PATENT NO.        : 8,939,074 B2  
APPLICATION NO.   : 13/796512  
DATED             : January 27, 2015  
INVENTOR(S)       : David P. Prince Page 1 of 1

It is certified that error appears in the above-identified patent and that said Letters Patent is hereby corrected as shown below:

In the Claims

Column 14, claim 1, line 48, before "substantially" add "light";

Column 14, claim 1, line 63, before "incident" add "is".

Signed and Sealed this  
Twenty-first Day of April, 2015

Michelle K. Lee  
*Director of the United States Patent and Trademark Office*